(12) United States Patent
White

(10) Patent No.: US 6,890,326 B2
(45) Date of Patent: May 10, 2005

(54) SANITARY SUPPLEMENT DEVICE

(76) Inventor: Sanette J White, 111 N. Third Ave., #7A, Mt. Vernon, NY (US) 10550

(*) Notice: Subject to any disclaimer, the term of this patent is extended or adjusted under 35 U.S.C. 154(b) by 114 days.

(21) Appl. No.: 10/242,958

(22) Filed: Sep. 12, 2002

(65) Prior Publication Data

US 2004/0054345 A1 Mar. 18, 2004

(51) Int. Cl.$^7$ ................................................ A61F 13/20
(52) U.S. Cl. ............................ 604/385.17; 604/385.01; 604/904; 604/11
(58) Field of Search ..................... 604/385.01, 385.17, 604/385.18, 904, 11–15

(56) References Cited

U.S. PATENT DOCUMENTS

| | | | | |
|---|---|---|---|---|
| 5,360,421 A | * | 11/1994 | Revelle | 604/378 |
| 6,313,371 B1 | * | 11/2001 | Conant et al. | 604/359 |
| 6,350,258 B1 | * | 2/2002 | Markowiecki | 604/385.201 |
| 6,652,503 B1 | * | 11/2003 | Bradley | 604/385.17 |

* cited by examiner

*Primary Examiner*—Jacqueline Stephens

(57) ABSTRACT

A sani-supplement device is disclosed, comprising an elongated body having a top portion, a middle portion and a bottom portion. The elongated body comprises an absorbent material. The top and middle portions are sized to be inserted into the crevice of the buttocks. The lower portion is placeable adjacent to the vagina, perhaps separated therefrom by a sanitary napkin. Alternatively, the lower portion may be placed directly against the vagina. In an alternate embodiment, the lower end region has a width larger than the width of the top and middle portions. A method is also disclosed for providing supplemental control over bodily fluids and/or other matter, comprising the steps of inserting the top and middle portion of the device into the crevice of the buttocks while leaving a lower portion of the sani-supplement hanging freely. A sanitary napkin is then applied to the pelvic area so that the sanitary napkin is adjacent to, in contact with, and at least partially overlapping a portion of the sani-supplement.

9 Claims, 2 Drawing Sheets

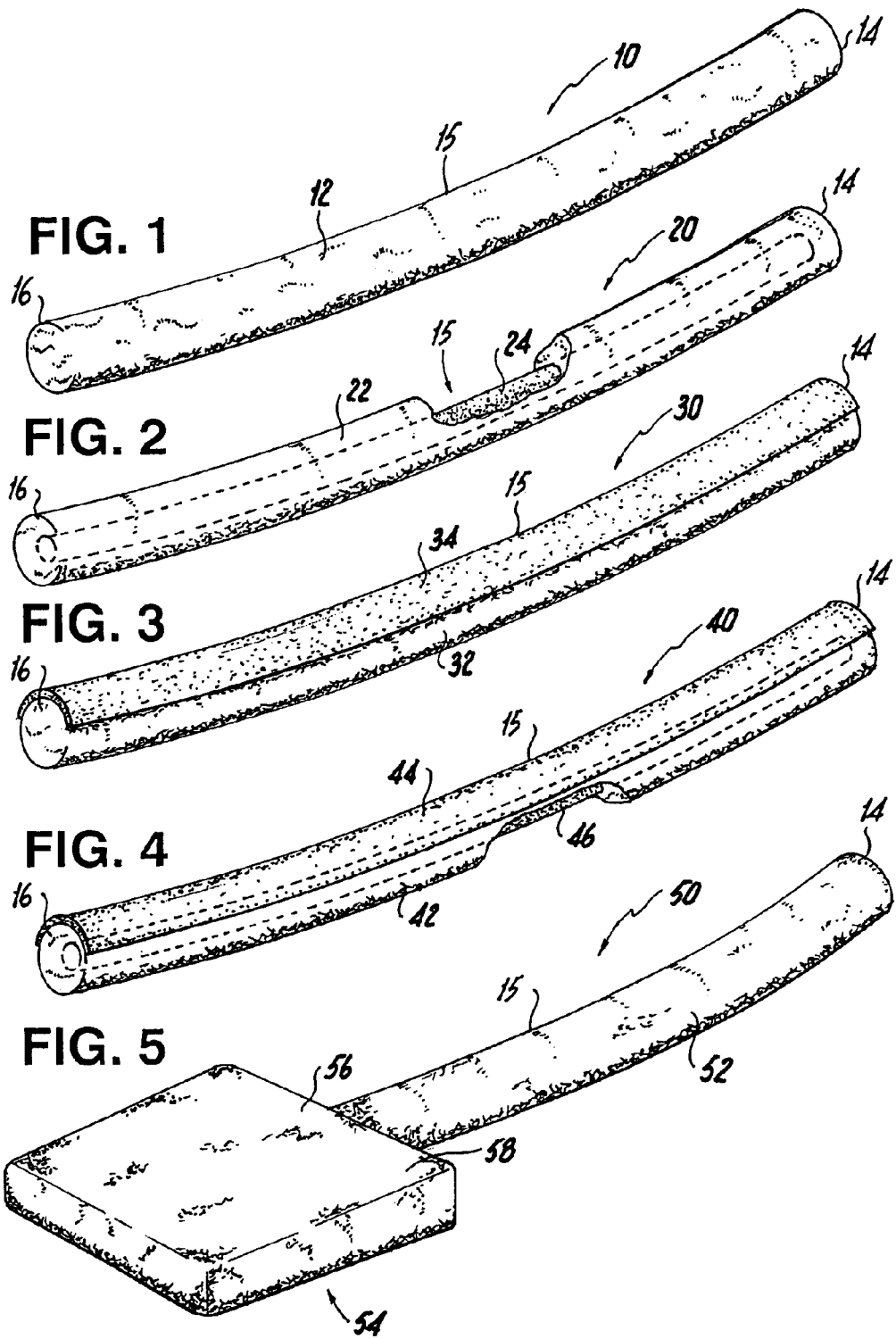

SANITARY SUPPLEMENT DEVICE

FIELD OF THE INVENTION

The present invention relates to a sanitary supplement device and method of use thereof, and in particular, to a sanitary supplement device, which may be utilized in conjunction with sanitary napkins and/or other sanitary products. The present invention may also be utilized by males, as well as females, to serve as a sanitary supplement.

BACKGROUND OF THE INVENTION

The development of sanitary napkins and related technologies and products dates back many years. Since the original development of sanitary napkin technology and products, there have been many improvements, including new and improved sanitary napkins and related absorbent materials. While sanitary napkins may prove sufficient for day wear, their use at night, either while resting or sleeping, presents problems of soiling and staining clothing, bedding and mattresses. This results from the uncontrolled flow of menstrual or other fluids. While tampons may be utilized by women at night, tampons may cause discomfort and overflow. In many cases, due to health reasons, tampons are not always recommended for use while sleeping. In view of the above shortcomings of the prior art, there exists a need for a sanitary supplement device and method of use thereof, which serves to overcome the shortcomings of the prior art and which provides for a novel apparatus and method for controlling the flow of menstrual 5 fluids and/or other matter while the user is in the horizontal position or while sleeping.

SUMMARY OF THE PRESENT INVENTION

The present invention is directed to a sanitary supplement device and method of use thereof which may be utilized in conjunction with sanitary napkins or related products so as to prevent an uncontrolled flow of menstrual fluids and/or other matter while a person is in a horizontal position, such as while asleep or while resting, so as to prevent soiling or staining of undergarments, clothing and/or bedding and bedding accessories. The product may be used by males, as well as females, to guard against uncontrolled seepage or secretion of bodily fluid and waste. Further, it may be used as a means to apply medication, medicaments and or salves.

The sanitary supplement device, (hereinafter referred to as the "sani-supplement") preferably includes an elongated cylindrical body or device, which is manufactured and/or comprised of an absorbent material. In the preferred embodiment, the absorbent material may be a cotton material. It is also important to note, however, that the sani-supplement may also be constructed of gauze, linen, and/or any other suitable absorbent material, e.g., gels. The sani-supplement may also come in any one or more of a wide variety of lengths, widths and/or diameters. All may be dictated by the physical size and shape characteristics of the user.

In a preferred embodiment, it is desirable that the sani-supplement be constructed of a highly absorbent material, which is capable of absorbing excess amounts of menstrual fluids, which may flow from the female user's body during her menstrual period and/or other matters (e.g., urine) which may flow from the body of a male or female user. In this regard, the material of the sani-supplement may also be chosen to be expansive as menstrual fluid or other seepage is absorbed.

The sani-supplement may also be constructed of any one of, or a combination of, a wide variety of known absorbent materials, such as the absorbent material that contains absorbent gels e.g., those that are commonly known and used in diapers, sanitary napkins and garments for the incontinent.

The sani-supplement may also comprise a plastic and/or a waterproof covering or backing which may be used to prevent leakage and/or spillage or seepage from and/or through the sani-supplement.

The sani-supplement device of the present invention may be utilized in the following manner so as to provide for the supplemental protection against the uncontrolled flow of menstrual fluids and/or other matter. The sani-supplement device may be used as a supplement to be used in conjunction with sanitary napkins and/or tampons.

The sani-supplement is applied to the user's body by inserting it lengthwise into the cavity or crevice between the user's buttock cheeks so that the top end of the sani-supplement is wedged within the cavity or crevice. The lower end of the sani-supplement should be left free hanging so that it can be placed adjacent to, in close proximity with, and/or in contact with the genitals and overlapped by a sanitary napkin or related product. In this manner, the sani-supplement will be positioned so as to absorb excess menstrual fluids and/or other matter which may flow from the body. These excess menstrual fluids and/or other matter may then be sufficiently absorbed and contained by the sani-supplement until its removal.

In the case of use and/or application in conjunction with a tampon, the lower portion of the sani-supplement may be placed adjacent to, or in close proximity with the vaginal opening or orifice so as to maximize the absorption of menstrual fluids and/or other matter while minimizing seepage or spillage of the same onto undergarments, clothing and/or bedding and bedding accessories.

Once applied to the buttocks cavity, the sanitary supplement will serve to collect, draw and absorb excess menstrual fluids and/or other matter which may secrete or flow from the user's body and which menstrual fluids and/or matter may not be collected and/or absorbed by the sanitary napkin and/or the tampon, whichever the case may be. In this regard, the sani-supplement serves to absorb excess menstrual fluids and/or other matter thereby preventing unwanted seepage and/or spillage of menstrual fluids and/or other matter thereby preventing the soiling and/or the staining of undergarments, clothing, bedding and/or bedding accessories.

After use, the sani-supplement may be removed and discarded at any time by the user, simply by removing the sani-supplement from the buttocks cavity or crevice 20 and disposing of same. The sani-supplement device of the present invention may be used during sleeping periods and/or during any other periods when a user may lie or be positioned in a horizontal manner, or is otherwise relatively motionless.

It is also important to note that the sani-supplement device may be easily adjusted and/or readjusted during wear by employing a similar and/or analogous insertion and/or removal procedure as described above.

In another alternate embodiment of the sani-supplement of the present invention, the sani-supplement is comprised of an elongated cylindrical body which is manufactured and/or comprised of an absorbent material which may be a cotton material. It is also important to note, however, that the sani-supplement may also be constructed of gauze, linen and/or any other suitable absorbent material.

The sani-supplement may also be comprised of an end section which is located at one end of the elongated cylindrical body. The end section has terminal portions which extend outwardly from the elongated cylindrical body so as to provide for an absorbent device which has an increased cross-sectional area. The end section defines the lower end portion of the sani-supplement for application purposes as will be described below.

The end section may have a rectangular, an oval, or any other suitable shaped cross-section. The end section may also be rounded or be circularly-shaped. The alternate embodiment sani-supplement may also comprise a covering or backing along a portion of its length and/or circumference and may further include an additional absorbent material.

When utilized, the alternate embodiment of the sani-supplement may be applied in a manner similar to, or analogous with, the manner of application which is described above. However, in the case of the alternate embodiment sani-supplement, the end section should be utilized as the lower portion of the sani-supplement so that it is placed adjacent to, in the region near, or be overlapped by, the sanitary napkin, as described above. In this manner, the sani-supplement provides for an end region, in the vicinity of, or adjacent to, the sanitary napkin which has a larger cross-sectional area for enhanced absorption capability of menstrual fluids and/or other matter.

The sani-supplement of the alternate embodiment may be removed, adjusted and/or readjusted during use in the manner as described above.

It is also important to note that the sani-supplement of the present invention may be utilized on males, as well as on females, in order to absorb other bodily waste fluids including seepage and/or secretions from the anal or rectal regions. The 10 sani-supplement device of the present invention may also be utilized as a means for applying and for retaining medication, medicaments and/or salves in the rectal, anal or buttocks region so as to prevent soiling and or seepage of the medication, medicament and or the salve, while keeping the same applied to the pertinent area and/or so as to prevent soiling and/or staining of undergarments, clothing, bedding and/or bedding accessories.

Accordingly, it is an object of the present invention to provide a sani-supplement device and method of use thereof which serves to control the flow of menstrual fluid and/or other matter which may occur when a user is in a horizontal position and/or while asleep.

It is another object of the present invention to provide a sani-supplement device and method of use thereof which serves to prevent and/or to control staining of undergarments, garments, bedding and/or bedding accessories.

It is another object of the present invention to provide a sani-supplement device that may be comprised of any one or more of a wide variety of absorbent materials.

It is a further object of the present invention to provide a sani-supplement device and method of use thereof, which may be utilized on males, as well as females, so as to prevent the uncontrolled flow of bodily fluids and/or waste matter.

Other objects and advantages of the present invention will be made apparent to those skilled in the art upon a review of the Description of the Preferred Embodiment taken in conjunction with the Drawings that follow.

BRIEF DESCRIPTION OF THE DRAWINGS

In the drawings:

FIG. 1 illustrates a preferred embodiment of the sani-supplement device which is the subject of the present invention;

FIG. 2 illustrates a perspective view of an alternate embodiment of the sanitary supplement of FIG. 1 with partial cutaway.

FIG. 3 illustrates a perspective view of another alternate embodiment of the sani-supplement device which is the subject of the present invention;

FIG. 4 illustrates an overall perspective of the sani-supplement device of FIG. 3 with a partial cutaway;

FIG. 5 illustrates yet another embodiment of the sani-supplement device which has a rectangular absorbent region for heavier use;

DESCRIPTION OF THE PREFERRED EMBODIMENT

Figure 6:
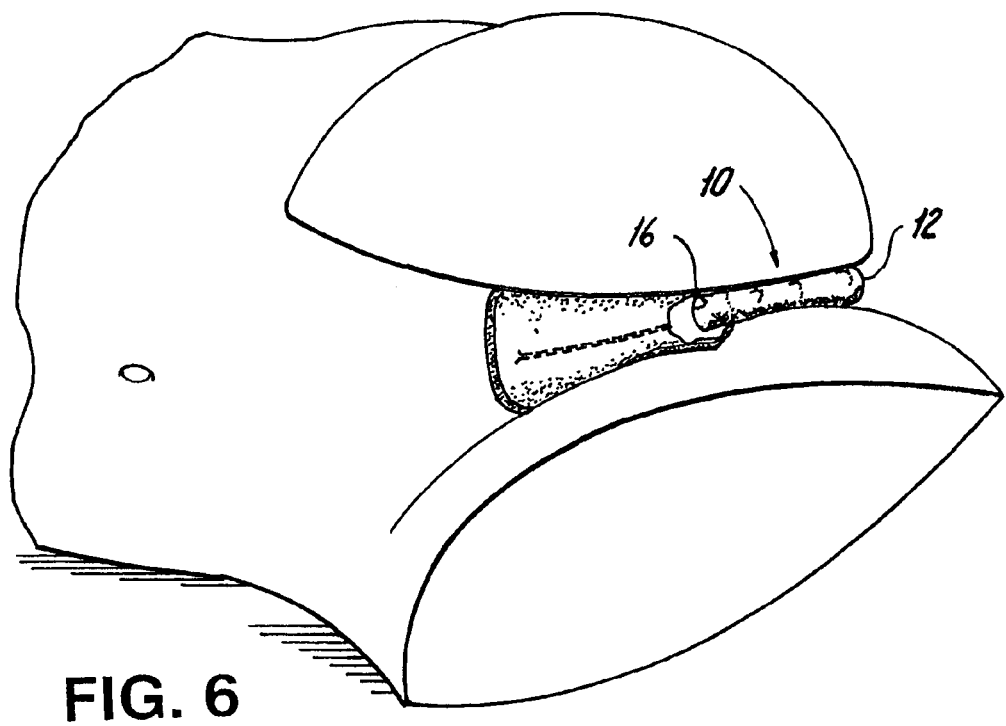
FIG. 6 illustrates a diagrammatic perspective view of the preferred embodiment installed in the crevice of the buttock and coming forward to the genital region.

FIG. 1 illustrates the sani-supplement device which is the subject of the present invention and which is denoted generally by the reference numeral 10. In FIG. 1, the sani-supplement device 10 is an elongated cylindrical device which is manufactured and/or comprised of an absorbent material which, in the preferred embodiment, is a cotton material 12. It should also be noted, however, that the sani-supplement 10 may be constructed or comprised of gauze, linen, or any other suitable absorbent material. The sani-supplement 10 may also come in any one or more of a wide variety of lengths, widths and/or diameters which may be dictated by the physical size and shape characteristics of the user.

In a preferred embodiment, the sani-supplement 10 can be constructed of a highly absorbent material which is capable of absorbing excess amounts of menstrual fluids, which may flow from a female user's body during her menstrual period and/or other matter that may flow from the bodies of male or female users. In this regard, the material of the sani-supplement 10 may also be chosen to be expansive as menstrual fluids and/or other matter is absorbed thereby.

The sani-supplement 10 may also be constructed of any one of, or a combination of, a wide variety of known absorbent materials, such as the absorbent materials that may contain and or consist of absorbent gels such as those which are commonly known and used in diapers, sanitary napkins and/or garments for the incontinent.

FIG. 2 illustrates an alternate embodiment of the sani-supplement of the present invention which is denoted generally by the reference numeral 20. In the sani-supplement 20 of FIG. 2, the sani-supplement 20 comprises absorbent material 22, which contains, in the center region thereof, an additional absorbent material 24 which may be any one or more suitable materials such as an absorbent gel, gauze, or any other suitable material. The additional absorption material 24 may be of any type or variety and may also be of a type such as those utilized in diapers, sanitary napkins, and/or garments for the incontinent.

FIG. 3 illustrates another alternate embodiment of the sani-supplement which is the subject of the present invention and which is denoted generally by the reference numeral 30. The sani-supplement 30 of FIG. 3 is constructed of an elongated cylindrical body 32 which is comprised of an absorbent material. The sani-supplement 30 of FIG. 3 also comprises a plastic and/or water-proof covering or backing 34, which may extend along a portion of the length and/or the circumference of the sani-supplement 30. The backing 34 prevents leakage and/or spillage or seepage from and/or through the sani-supplement 30.

FIG. 4 illustrates another alternate embodiment of the sani-supplement device which is the subject of the present invention, and which is denoted generally by the reference numeral 40. The sani-supplement 40 of FIG. 4 comprises an elongated cylindrical body 40 which is comprised of an absorbent material and a covering or backing 44 which surrounds a portion of the circumference and/or a portion of the length of the elongated cylindrical body 40. The sani-supplement device 40 of FIG. 4 further comprises an additional absorbent material 46 which may be any one or more of a wide variety of suitable materials such as an absorbent gel, gauze, and/or other suitable material. such as those utilized in diapers, sanitary napkins, and/or garments for the incontinent.

It is important to note that the materials which are utilized in any of the above-described and/or below-described embodiments of the sanitary supplement device of the present invention may or should be chosen so that they can provide maximum absorption with minimum expansion.

The sani-supplement device of the present invention may be utilized to provide protection against the uncontrolled flow of menstrual fluids and/or other matter. In the preferred embodiment, the sani-supplement device, which is the subject of the present invention, should be used in conjunction with sanitary napkins or products. In the preferred embodiment, the sanitary supplement device is used in conjunction with sanitary napkins.

FIG. 5 illustrates a view wherein the sani-supplement device has a rectangular end section 54 for heavier use. The use and/or application of the sani-supplement device of FIG. 5 will be described below in connection with and illustrated in FIG. 7.

The sani-supplement devices of FIGS. 1–4 are applied to the user's body by inserting one of them lengthwise into the cavity or crevice between the user's buttocks so that the top end 14 and middle region 15 of the sani-supplement is wedged within the cavity or crevice. The lower end 16 of the sani-supplement should be left free-hanging.

FIG. 6 illustrates a diagrammatic view of a female pelvic and/or lower torso region with a sani-supplement device fully applied. As shown in FIG. 6, the sani-supplement device should be placed so that an ample length of same at the lower portion 16 thereof remains in the pelvic, and/or lower torso region, as shown. The lower portion of the sani-supplement 10, should be left free hanging so that it can be placed adjacent to or in close proximity with the genital region of the user, and/or can be overlapped with or by, a sanitary napkin, once the sanitary napkin has been applied in a usual manner. As shown in FIG. 6, the lower portion of the sani-supplement device 10 is placed so that it is overlapped by a sanitary napkin (shown in dotted line).

In the case of use and/or application in conjunction with a tampon, the lower portion of the sani-supplement 10 may be placed adjacent to, or in close proximity with, the vaginal opening or orifice so as to maximize the absorption of menstrual fluids and/or other matter while minimizing seepage or spillage of same onto undergarments, clothing and bedding and/or bedding accessories.

Once applied to the body, the sani-supplement 10 will serve to collect, draw and absorb excess menstrual fluids and/or other matter which may secrete or flow from the user's body, which fluids and/or other matter may not be collected and/or absorbed by the sanitary napkin and/or the tampon, whichever the case may be. In this regard, the sani-supplement 10 serves to absorb excess menstrual fluid and/or other matter thereby preventing unwanted seepage and/or spillage of menstrual fluids and/or other matter thereby preventing the soiling and/or the staining of, undergarments, clothing, bedding and/or bedding accessories.

After use, the sani-supplement may be removed and discarded at any time by the user, simply by removing the sani-supplement from the buttocks cavity or crevice and disposing of same. The sani-supplement device 10 of the present invention is used fro sleeping periods and/or during any other time when a user is in a horizontal position or is otherwise relatively motionless.

It is also important to note that the sani-supplement device may be easily adjusted and/or readjusted during wear by employing similar insertion and/or removal procedures as described above.

Figure 7:
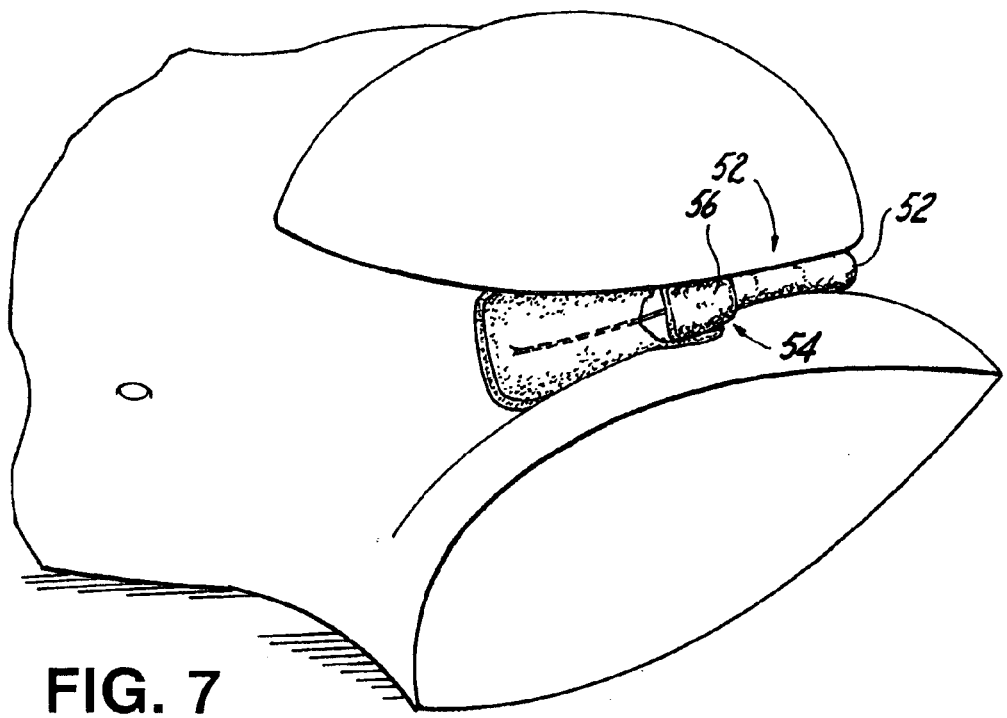
FIG. 7 illustrates a diagrammatic perspective view of the preferred embodiment of FIG. 5 installed in the crevice of the buttock and coming forward to the genital region.

FIG. 7 illustrates another alternate embodiment of the sani-supplement device of the present invention which is denoted generally be reference numeral 50. In FIG. 7, the sani-supplement device 50 (which is shown in more detail in FIG. 5), is comprised of an elongated cylindrical body 52 which is manufactured and/or comprised of an absorbent material which, in the preferred embodiment, is manufactured from cotton material. It is also important to note, however, that the sani-supplement 50 of FIG. 7 may also be constructed of gauze, linen and/or any other suitable absorbent material.

In FIG. 7, the sani-supplement 50 is also comprised of an end section 54 which is located at one end of the elongated cylindrical body 50. The end section 54 has lateral portions 56, 58 as shown, which extend outwardly from the elongated cylindrical body 50 to provide for an absorbent device which has an increased cross-section area. The end section 54, as shown in FIG. 5 has a rectangular shaped cross-section. It is important to note, however, that the end section 54 may be of an oval cross-sectional shape and/or may be of any other suitable cross-section shape.

In the case of the sani-supplement 50, the end section 54 should be utilized as the lower portion of the sani-supplement 50 so that it is placed adjacent to, in the region near, or be overlapped by the sanitary napkin, as described above and as illustrated in FIG. 7. In this manner, the sani-supplement 50 provides for an end region in the vicinity of, or against, the sanitary napkin that has a larger cross-sectional area for enhanced absorption of menstrual fluids and/or other matter.

The sani-supplement 50 may be removed, adjusted and/or readjusted during use, in the manner described above for the application and/or for the removal of the sani-supplement.

It is also important to note that the sani-supplement of the present invention may also be utilized on males, as well as on females, in order to absorb other bodily fluids and/or waste matter and/or including seepage and/or secretions in the anal regions. The sani-supplement device of the present invention may also be utilized as a means for applying and for retaining medication, medicaments and/or salves in the anal, region so as to prevent soiling and or seepage of the medication, medicament and or salve, while keeping same applied to the pertinent area and/or to prevent soiling and/or staining of undergarments, clothing, bedding and/or bedding accessories.

While the present invention was shown and described with reference to a preferred embodiment, various modifications thereof will be apparent of those skilled in the art and, therefore is not intended that the invention be limited to the disclosed embodiments and/or details thereof, and departure may be made therefrom within the spirit and scope of the appended claims.

What is claimed is:

1. A sanitary supplement device which comprises:
   an elongated body which comprises:
   a top portion;
   a middle portion;
   a lower portion;
   wherein said elongated body is comprised of an absorbent material, wherein said top portion and said middle portion are adapted to be inserted into the cavity or crevice of the buttocks, and further wherein said lower portion is free of attachment to an undergarment and is adapted to be placed one of adjacent to, and against the genitals.

2. The sanitary supplement device of claim 1, wherein the elongated body is cylindrical in shape.

3. The sanitary supplement device of claim 1, wherein said elongated body is comprised of an absorbent material.

4. The sanitary supplement device of claim 3, wherein said absorbent material is one or more of a cotton material, a gauze, and a linen, material.

5. A sanitary supplement device which comprises:
   an elongated body which comprises:
   a top portion;
   a middle portion; and
   a lower portion, wherein said lower portion has a width which is larger than the width of at least one of said top portion and said middle portion;
   wherein said elongated body is comprised of an absorbent material, wherein said top portion and said middle portion is adapted to be inserted within the crevice of the buttocks, and further wherein said lower portion is free of attachment to an undergarment and is adapted to be placed one of adjacent to and against the genitals.

6. The sanitary supplement device of claim 5, wherein the elongated body is cylindrical in shape.

7. The sanitary supplement device of claim 5, wherein said absorbent material is one or more of a cotton material, a gauze, and a linen material.

8. The sanitary supplement device of claim 5, wherein said lower portion has one of a rectangular and an oval shaped cross section.

9. A method for providing supplemental control over a flow of bodily fluids and/or other matter which comprises the steps of:
   inserting a top and a middle portion of a sani-supplement device into the crevice of the buttocks while leaving a lower portion of said sani-supplement hanging freely; and
   applying a sanitary napkin to the pelvic area so that the sanitary napkin is at least one of adjacent to, in contact with, and at least partially overlaps said lower portion of said sani-supplement.

* * * * *